United States Patent [19]
Carew

[11] Patent Number: 4,807,991
[45] Date of Patent: Feb. 28, 1989

[54] METHOD OF INSPECTING AND REPAIRING A STRUCTURAL DEFECT IN THE SURFACE OF AN OBJECT

[75] Inventor: Evan B. Carew, Dearborn, Mich.

[73] Assignee: Electro-Organic Company, Dearborn, Mich.

[21] Appl. No.: 848,606

[22] Filed: Apr. 7, 1986

[51] Int. Cl.$^4$ .................... G01N 21/64; G01N 21/65; G01N 21/88

[52] U.S. Cl. ................. 356/72; 219/121.83; 219/121.85; 356/312; 356/328; 356/237

[58] Field of Search ............ 356/237, 239, 301, 318, 356/328, 72; 219/121 LZ, 121 LB, 121 LW, 221 LM

[56] References Cited

U.S. PATENT DOCUMENTS

| | | | |
|---|---|---|---|
| 4,195,930 | 4/1980 | Delhaye et al. | 356/301 |
| 4,316,074 | 2/1982 | Daly | 219/121 LB |
| 4,397,556 | 8/1983 | Muller | 356/301 |
| 4,407,008 | 9/1983 | Schmidt et al. | 356/301 X |
| 4,573,761 | 3/1986 | McLachlan et al. | 356/301 X |
| 4,586,819 | 5/1986 | Tochigi et al. | 356/301 |

FOREIGN PATENT DOCUMENTS 60-53834  3/1985  Japan ................. 356/301

Primary Examiner—Vincent P. McGraw
Attorney, Agent, or Firm—Cullen, Sloman, Cantor, Grauer, Scott & Rutherford

[57] ABSTRACT

A method and apparatus are provided for mapping the surface morphology of an object in order to detect and repair structural defects in the object or to distinguish surface features. A beam of light having a single frequency, such as a laser, is scanned across a plurality of locations on the object's surface and the light reflected from each surface location is received and analyzed by a spectrometer and a multi-channel analyzer. The reflected light originating from the laser beam which is absorbed by the surface is shifted in frequency by an amount determined by the type and concentration of molecular bonding of the surface material. The type and concentration of bonding for each scanning location is represented by a set of binary data which are then used to generate a composite visual display of the surface in which each pixel has a color and intensity determined by the set of binary data which represent the type and concentration of bonding. The visually displayed bonding pattern reveals surface defects, surface features, anomalies, etc. Display sensitivity is increased by tuning the energy of the incident laser to the energy gap between the ground state and excited state of the electrons of the surface material. The power of the laser beam employed for inspection can be increased to anneal and thereby repair surface defects.

2 Claims, 3 Drawing Sheets

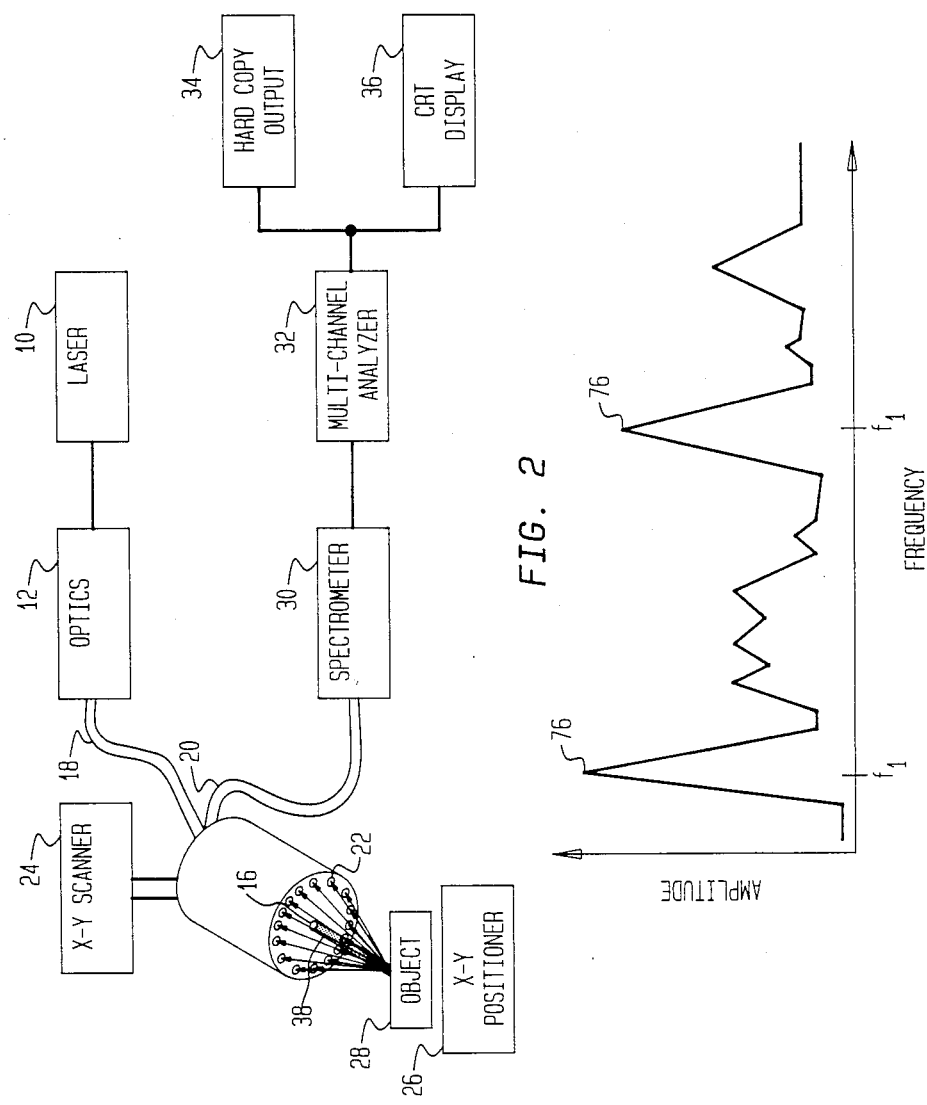

METHOD OF INSPECTING AND REPAIRING A STRUCTURAL DEFECT IN THE SURFACE OF AN OBJECT

TECHNICAL FIELD

The present invention broadly relates to systems for scanning the surface of an object in order to detect or repair defects, and deals more particularly with a method and apparatus for mapping the morphology of a surface in order to produce a visual display of molecular bonding patterns which reveal surface defects.

BACKGROUND ART

Various types of inspection systems have been devised in the past which use a visual scanning technique for determining the location of a defect or anomaly in the surface of an object. Such a system typically employs a conventional television camera which receives reflected light from the object's surface which is then converted to a display. Pattern recognition techniques are employed to scan the displayed image in order to locate the defect.

Many types of defects are not readily visually perceivable and therefore cannot be detected with conventional visual scanning techniques. For example, poor molecular bonding in a defective weld may not be revealed at the surface of the weld. In the field of gaging, visual scanning techniques which rely on differences in grey scale level to distinguish features are ineffective in thoses cases where adjacent but different features are the same color and intensity.

It is known that the amount of light energy absorbed by a material is dependent upon the type of bonding within the molecules which make up the material and that light reflected from such material is shifted in energy or wavelength by an amount commensurate with the type and concentration of molecular bonding. Others have used this principle in the past to identify the constituent elements of a material. That is to say, others have used a technique to identify the constituent elements of a material in which a beam of light of a known frequency was directed onto the surface of the material and the shift in frequency of the reflected light from the material was measured in order to identify the constituent elements. It is also known that sensing sensitivity may be increased by tuning the energy of the incident light beam to that of the energy gap of the material being inspected. This latter technique is sometimes referred to as resonance Roman spectroscopy.

SUMMARY OF THE INVENTION

According to the present invention, a method and apparatus are provided for mapping the surface morphology of an object in order to detect structural defects in the object and/or detect and distinguish surface features. A beam of light having a single frequency, such as a laser, is directed onto the surface of the object and is then scanned across a plurality of points or locations on the object's surface. Light reflected from the surface at each scanned location is received and analyzed using a spectrometer and a multi-channel analyzer. The spectrometer separates randomly scattered light from that reflected light originating from the laser beam. The separated spectrum of reflected light is directed onto a linear array of photosensitive elements as a function of frequency. The reflected light originating from the laser beam which is absorbed by the object's surface is shifted in frequency by an amount determined by the type and concentration of molecular bonding of the surface materials. The multi-channel analyzer converts the spectrum of sensed energies to a set of binary data representing the type and concentration of bonding. The binary data is stored in memory and may be recalled to generate a composite visual display of the surface in which each pixel has a color and intensity determined by the set of binary data which represent the type and concentration of the bonding. The visual bonding pattern reveals surface defects, anomalies, differences in surface features, etc. The sensitivity of the method is substantially increased by tuning the energy of the incident laser to the energy gap between the ground state and the excited state of the electrons of the surface material. In order to repair a surface defect, the laser which is employed to perform the inspection process is also used at an increased power level to anneal the surface defect and thereby repair the surface.

Accordingly, it is a primary object of the present invention to provide a device-implemented method for mapping the surface morphology of an object for the purpose of detecting or repairing structural defects in the object, or determining surface features of an object for purposes of gaging or the like.

Another object of the invention is to provide a device implemented method as described above which employs resonance Raman spectroscopy in order to increase the sensitivity with which the type and concentrations of molecular bonding are sensed.

A still further object of the invention is to provide a device implemented method as described above in which the patterns of molecular bonding of the constituent elements of the object's surface are displayed in a pattern which reveals the concentration of such bonding and any defects or anomalies in the surface material.

These, and further objects of the invention, will be made clear or will become apparent during the course of the following description of a preferred embodiment of the present invention.

BRIEF DESCRIPTION OF THE DRAWINGS

In the drawings, which form an integral part of the specification and are to be read in conjunction therewith, and in which like reference numerals are employed to designate identical components in the various views:

FIG. 1 is a combined diagrammatic and broad block view of the system which forms the preferred embodiment of the present invention;

FIG. 2 is a plot of the spectrum of energies of the frquency shifted light reflected from the object's surface;

DESCRIPTION OF THE PREFERRED EMBODIMENTS

Figure 3:
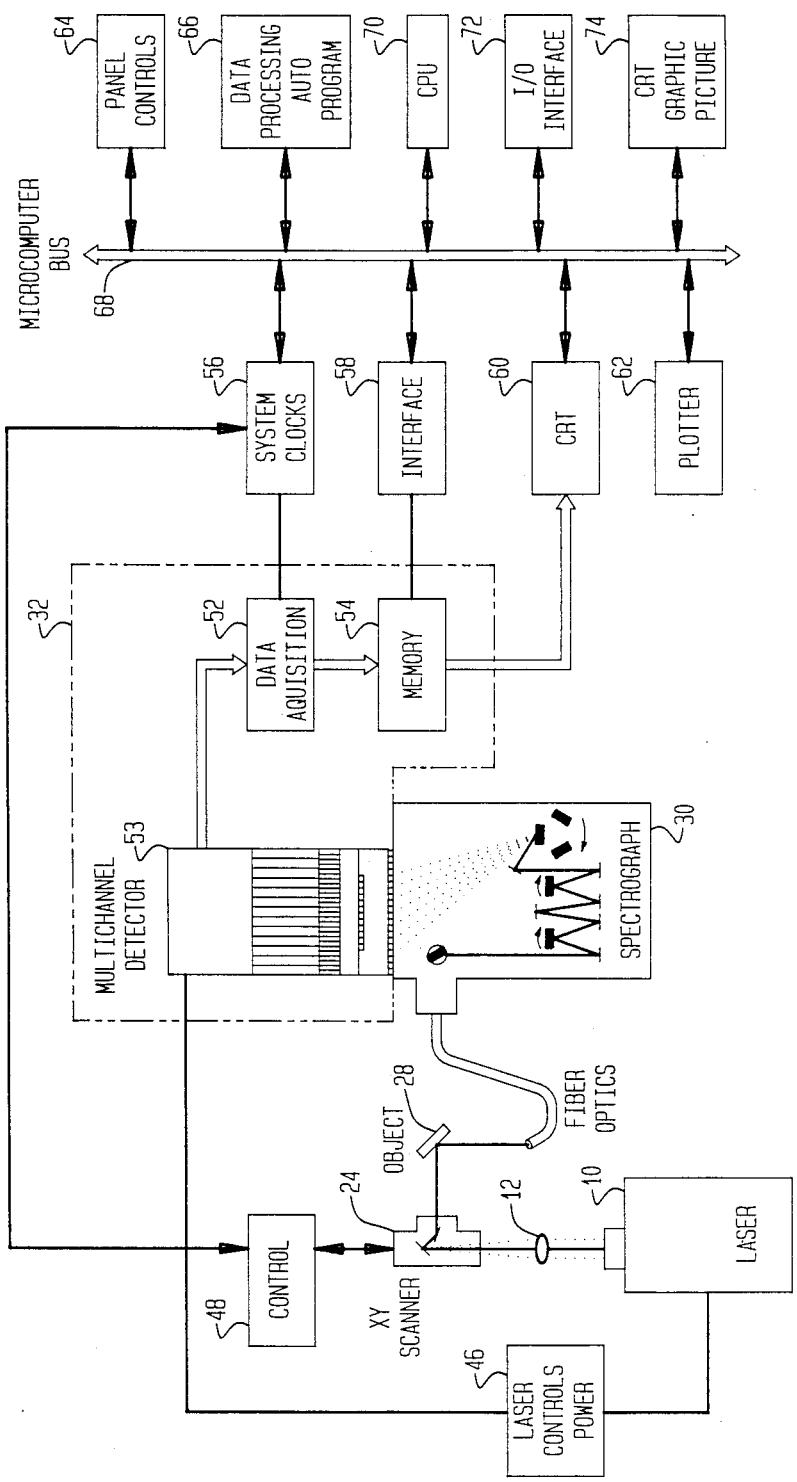
FIG. 3 is a detailed block diagram of the system shown in FIG. 1.

Referring first to FIG. 1, the present invention is broadly concerned with a device implemented method for mapping the surface morphology of an object in order to detect and repair structural defects in an object. The term "morphology" as used herein is intended to mean the chemical make-up, and particularly the type and concentration of molecular bonding of a material. The term "surface" morphology is intended to refer to the nature or character of the bonding between the first few layers of molecules in the surface of an object. By obtaining information relating to the type and concentration of molecular bonding in the first few layers of molecules, generalizations can be made regarding the presence and nature of surface defects which apply to the structural integrity of the material below the first few molecular layers. By determining the surface morphology at a plurality of points on the object's surface, a map can be formed of the distribution of elements on such surface. This information can then be readily interpreted to identify defects, to determine surface topology and to distinguish surface features for purposes of gaging or the like.

The present invention takes advantage of the fact that certain constituent elements, and particularly the character of the bonds between the molecules of such elements, determine whether light energy impinging thereon is absorbed or is reflected. If the energy level of the incident light is reduced, the collision between the photons and the molecules is said to be inelastic. Consequently, the photons loose a portion of their momentum, thus decreasing the energy of the light. If a material is bombarded with a beam of light having a single frequency, the light reflected from the surface of such material will be at a lower frequency or longer wavelength, with the frequency shift being determined by the type and concentration of molecular bonding of the material's surface. This frequency shift is substantially exaggerated if the energy level of the incident light beam is tuned to or closely matches the energy gap between the ground state and the excited state of the electrons of the surface material. The enhancement of frequency shift using this technique can be between $10^6$ or $10^8$, consequently detection sensitivity is substantially increased. Hereinafter, the term resonance will be used to refer to the energy matching between the incident light beam and the energy gap of the electrons in the surface material.

As shown in FIG. 1, a conventional laser 10 is employed which provides a laser beam in the desired frequency range so as to achieve resonance with the energy gap of the electrons of the material to be bombarded. In the case of a metal substrate, for example, an ultraviolet laser may be employed since the metal oxide bonds have electronic and vibronic ban gaps in the ultraviolet frequency range. The laser 10 preferably has a variable power level between one watt and 30 to 50 watts so as to function as a beam source which can be used both to inspect and repair the surface of an object 28. One suitable laser is a pulsed ultraviolet device available from the Lambda Physik Company.

Figure 4:
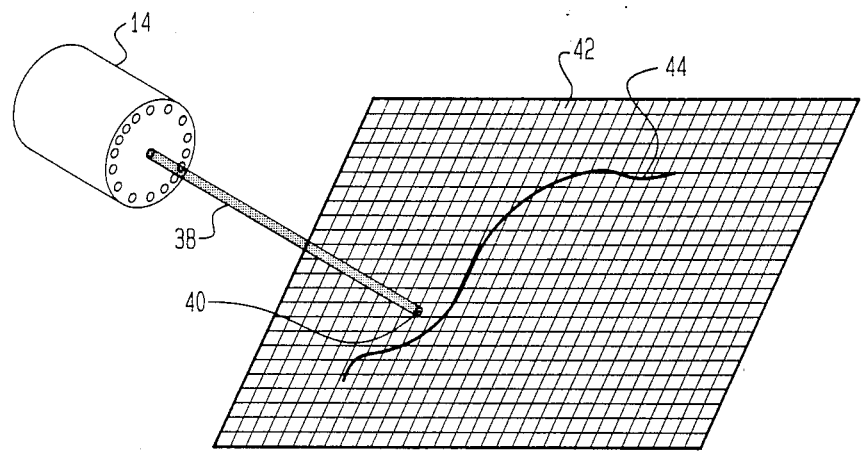
FIG. 4 is a perspective, diagrammatic view of the surface of an object having a defect therein which is being scanned by the probe of the system; and, FIG. 5 is a plan view of a typical display of the morphology of the surface of an object which has been mapped according to the present invention.

The output beam from the laser 10 is delivered to a set of conventional optics 12 which function to focus the laser beam, and the focused beam is transferred by means of a bundle of optical fibers 18 to a probe 14. The bundle of optical fibers 18 is mounted on the probe 14 so as to be centrally disposed at 16. The resulting, focused laser beam 38 may be 0.1 to 100 microns in diameter, and as shown in FIG. 4, impinges the surface 42 of the object 28 at discrete locations dependent upon the relative positions of the probe 14 and the surface 42. Relative movement is effected between the probe 14 and the object 28 such that the laser beam 38 successively scans a pattern of points or locations as at 40 across the surface 42. For convenience, the locations to be scanned are shown in a grid pattern in FIG. 4 in contemplation of raster scanning, however it is to be understood that various other patterns and schemes for scanning can be used. In order to effect scanning, an XY scanner 24 is employed to move the probe 14 relative to the object 28. However, if desired, the probe 14 can be stationarily mounted and the object 28 may be mounted on an XY positioner 26 such as a table which then moves the object 28 relative to the probe 14. In any event, the light reflected from the bombarded surface 42 of the object 28 is received by a plurality of optical pick-ups 22 which are equally circumferentially spaced on the probe 14, around the point of emanation 16 of the laser beam 38. The optical pick-ups 22 each comprise a bundle of optical fibers and a lens (not shown) which concentrates and focuses the reflected light energy into the corresponding optical fiber bundle. The optical fiber bundles of the pick-ups 22 are collectively shown by the cable 22 which is connected with a spectrometer 30.

The optical pick-ups 22 receive both reflected light originating from the laser beam 38 as well as randomly scattered light. The spectrometer 30 is a conventional device such as that manufactured by Spex Industries which functions to separate the reflected (elastic) from the non-reflected (inelastic) light. The output of the spectrometer 30 is a spectrum of energy for each location 40 on the surface 42. An example of the energy spectrum output from the spectrometer 30 is depicted in FIG. 2 which plots the energies as a function of amplitude and frequency. This plot represents the energies contained in the frequency shifted light reflected from the surface 42 of the object which originate from the laser beam 38. By way of example, the peak of highest amplitude 76 at frequency $f_1$ may represent the molecular bonds of a heavy metal while the peak 78 of second highest amplitude at frequently $f_2$ may represent lighter metals for example. Thus, each of the peaks of the plot of FIG. 2 is characteristic of an energy corresponding to a particular type of molecular bonding.

The multi-channel analyzer 32 is also a conventional device manufactured by Trecor Northern which functions to convert selected points or frequencies in the energy spectrum output by the spectrometer 30 into a set of digital data which represent the frequency and amplitude of the bonding energy. The analyzer 32 additionally assigns a color to each frequency of interest as well as a color intensity corresponding to the amplitude of the energy at the selected frequency. The analyzer 32 thus stores a set of data in memory for each location which is scanned on the surface 42 of the object 28. This latter-mentioned set of data is retrieved from memory by the analyzer 32 and is employed to generate a visual display of the molecular bonding concentrations of the surface material, wherein the nature of each constituent element is represented by a color and the amount or concentration of that element corresponds to the intensity of the color.

Additional details of the system of FIG. 1 are shown in FIG. 3. The laser 10 is provided with conventional laser power controls 46 which are in turn controlled by the multi-channel analyzer 32. The XY scanner 24 may comprise conventional piezoelectric drivers and rotating mirrors of the type readily available from Burleigh Instruments. The scanner 24 is operated by a conventional control 48 which in turn is controlled by the analyzer 32. The analyzer 32 may include a memory stored conventional algorithm (software) which functions to compensate for paralax created by the scanner 24.

The spectrometer 30 includes a plurality of gratings through which the incoming light is scattered in order to separate the energies into an energy spectrum. The separated energy spectrum is then focused from the last grating onto a linear photodiode array 50 which senses the presence and magnitude of energy at differing frequencies. The analyzer 32 includes a multi-channel detector 53 for sensing the frequency and amplitude of each energy level. The frequency and amplitude of each detected energy is processed by a data acquisition system 52 and is stored in a memory 54 as a function of the particular location or point 40 on the surface 42 of the object 28.

Figure 5:
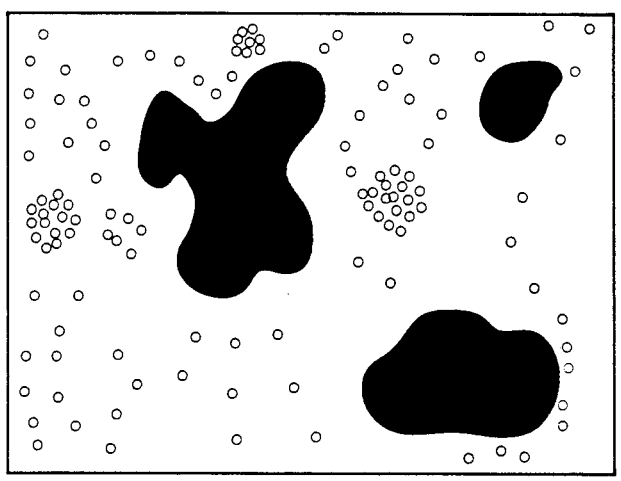

A microcomputer including a CPU 70 is provided for controlling the XY scanner and the multi-channel analyzer 32 so as to coordinate the acquisition of data regarding the detected energies with the location being scanned. The microcomputer includes conventional components such as system clocks 56, an interface 58 connecting a microcomputer bus 68 with the memory 54, a CRT 60, plotter 62, control panel 64, an automatic data processing program 66, an input/output interface 72 and a graphics generator 74. The microcomputer assigns a color and a color intensity to the set of data stored in the memory 54. Additionally, the operator may select the particular energy (a bonding type) to be analyzed. Thus, if it is desired to produce a display of the energies represented by the peaks 76, 78 in FIG. 2, the microcomputer would assign a color and corresponding intensity to each one of these energies at each scanned location. Under control of the microcomputer, a visual display would be produced either by the CRT 60 or plotter 62 which represents a map of the constituent elements and their concentrations, with each pixel of the display corresponding to a scanned location on the surface 42 of the object 28. A typical visual display of a map of the morphology of a surface is shown in FIG. 5.

Having displayed the patterns of the constituent elements and their concentrations, such display will reflect any defects in the surface morphology of the object 28, such as a crack or fissure 44 shown in FIG. 4. The coordinate locations of the crack 44 may be loaded into memory of the microcomputer so that its position on the surface 42 is known. The crack 44 may be repaired by increasing the power of the laser 10 to the required level, typically 40 to 50 watts. The laser beam 38 is then employed to trace the crack 44, thereby changing the phase of the constituent elements and annealing the material to repair the crack.

Moreover, the displayed patterns or "maps" of the constituent elements and their concentrations provide information which can be used to determine the topology of the surface 42 and can be used to distinguish different surface features on an object; thus, the surface morphology map can be employed in pattern recognition and gaging applications to determine the presence and location of surface features.

Having thus described the invention, it is recognized that those skilled in the art may make various modifications or additions to the preferred embodiment chosen to illustrate the invention without departing from the spirit and scope of the present contribution to the art. Accordingly, it is to be understood that the protection sought and to be afforded hereby should be deemed to extend to the subject matter claimed and all equivalents thereof fairly within the scope of the invention.

What is claimed is:

1. A method of inspecting and repairing a structural defect in the surface of an object, comprising the steps of:

identifying the defect in the surface of said object by
(1) directing a beam of light from a laser onto the surface of said object, the light reflected from said surface and originating from said laser being shifted in frequency by an amount determined by the morphology of the structure of said surface,
(2) scanning a plurality of locations on said surface using said laser light beam,
(3) receiving the light reflected from each surface location scanned in step (2), and
(4) analyzing the shift in frequency of light received in step (3) to determine the location of a defect in said surface structure; and repairing the defect in said surface structure by
(5) increasing the power of said laser light beam to a level sufficient to effect a phase change in said surface structure, and
(6) directing said laser light beam onto the defect, whereby to effect a phase change in the surface structure of said object at the location of the defect.

2. The method of claim 1, including the steps of:
reducing the power of said laser light beam after the defect is repaired, and
inspecting the location of the surface which has been repaired in steps (5) and (6) by directing the laser light beam onto the surface location of the repair, receiving the light reflected from the surface of the object and analyzing the shift in frequency of the received light to determine whether the defect has been repaired.

* * * * *